United States Patent
Van Der Heide et al.

(10) Patent No.: US 9,745,234 B2
(45) Date of Patent: Aug. 29, 2017

(54) PROCESS FOR THE PREPARATION OF GLYCOLS

(71) Applicant: SHELL OIL COMPANY, Houston, TX (US)

(72) Inventors: Evert Van Der Heide, Amsterdam (NL); Pieter Huizenga, Amsterdam (NL); Govinda Subbanna Wagle, Bangalore (IN)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 14/914,037

(22) PCT Filed: Aug. 22, 2014

(86) PCT No.: PCT/EP2014/067885
§ 371 (c)(1),
(2) Date: Feb. 24, 2016

(87) PCT Pub. No.: WO2015/028398
PCT Pub. Date: Mar. 5, 2015

(65) Prior Publication Data
US 2016/0207856 A1 Jul. 21, 2016

(30) Foreign Application Priority Data
Aug. 26, 2013 (EP) .................... 13181707

(51) Int. Cl.
| | | |
|---|---|---|
| *C07C 29/132* | (2006.01) |
| *C07C 29/60* | (2006.01) |
| *C07C 31/20* | (2006.01) |
| *B01J 23/46* | (2006.01) |
| *B01J 21/06* | (2006.01) |
| *B01J 23/89* | (2006.01) |
| *B01J 21/08* | (2006.01) |
| *B01J 23/28* | (2006.01) |
| *B01J 23/30* | (2006.01) |

(52) U.S. Cl.
CPC ........... *C07C 29/132* (2013.01); *B01J 21/066* (2013.01); *B01J 21/08* (2013.01); *B01J 23/28* (2013.01); *B01J 23/30* (2013.01); *B01J 23/462* (2013.01); *B01J 23/8993* (2013.01); *C07C 29/60* (2013.01); *Y02P 20/52* (2015.11)

(58) Field of Classification Search
CPC ... C07C 31/202; C07C 31/205; C07C 29/132; C07C 29/60; C07C 31/207; B01J 23/462; B01J 21/066; B01J 23/8993; B01J 23/30; B01J 23/2821
See application file for complete search history.

(56) References Cited

U.S. PATENT DOCUMENTS

| | | | |
|---|---|---|---|
| 4,366,332 A | 12/1982 | Chao et al. |
| 4,417,972 A | 11/1983 | Frances et al. |
| 4,473,459 A | 9/1984 | Bose et al. |
| 4,476,331 A | 10/1984 | Dubeck et al. |
| 4,628,128 A | 12/1986 | Bartley |
| 5,600,028 A | 2/1997 | Gubitosa et al. |
| 6,291,725 B1 | 9/2001 | Chopade et al. |
| RE39,073 E * | 4/2006 | Herbolzheimer .......... B01J 8/22 518/700 |
| 2010/0019191 A1 * | 1/2010 | Hoffer .................... C07C 29/00 252/70 |
| 2011/0046419 A1 | 2/2011 | Zhang et al. |
| 2011/0313212 A1 | 12/2011 | Kalnes et al. |
| 2013/0165698 A1 * | 6/2013 | Powell .................... C10G 3/00 568/863 |

FOREIGN PATENT DOCUMENTS

| | | |
|---|---|---|
| CN | 102643165 | 8/2012 |
| CN | 102675045 | 9/2012 |
| CN | 102731259 | 10/2012 |
| CN | 103731258 | 4/2014 |
| EP | 2348136 | 7/2011 |
| GB | 2478332 | 9/2011 |
| WO | 2012174087 | 12/2012 |
| WO | 2013015955 | 1/2013 |
| WO | 2015028398 | 3/2015 |
| WO | 2015097096 | 7/2015 |

OTHER PUBLICATIONS

Ji, Na: Direct Catalytic Conversion of Cellulose into Ethylene Glycol Using Nickel-Promoted tungsten Carbide Catalysts, Biomass Conversion, Angew. Chem. Int. Ed. 2008, 47, pp. 8510-8513.
Dhepe, Parish, L., et al.: Cracking of cellulose over supported metal catalysts, Catalysis Surveys From Asia, vol. 11, No. 4, Oct. 25, 2007, pp. 186-191, XP019549489.

* cited by examiner

*Primary Examiner* — Jafar Parsa

(57) ABSTRACT

The invention provides a process for the preparation of ethylene glycol and 1, 2-propylene glycol from starting material comprising one or more saccharides, wherein the process comprises the steps of i) providing the starting material and hydrogen to a first reactor, which first reactor operates with mixing; ii) reacting said starting material and hydrogen in the first reactor in the presence of solvent and a catalyst system; iii) continuously removing a first reactor product stream from the first reactor; iv) supplying at least a portion of the first reactor product stream to a second reactor, which reactor operates essentially in a plug flow manner; and v) further reacting the first reactor product stream with hydrogen in the presence of a solvent and optionally a catalyst system in the second reactor.

9 Claims, No Drawings

PROCESS FOR THE PREPARATION OF GLYCOLS

PRIORITY CLAIM

The present application is a National Stage (§371) application of PCT/EP2014/067885, filed Aug. 22, 2014, which claims priority from European patent application 13181707.4 filed 26 Aug. 2013, each of which are hereby incorporated by reference in their entirety.

FIELD OF THE INVENTION

The present invention relates to a process for the preparation of ethylene and propylene glycols from saccharide-containing feedstock.

BACKGROUND OF THE INVENTION

Ethylene glycol and propylene glycol are valuable materials with a multitude of commercial applications, e.g. as heat transfer media, antifreeze, and precursors to polymers, such as PET. Ethylene and propylene glycols are typically made on an industrial scale by hydrolysis of the corresponding alkylene oxides, which are the oxidation products of ethylene and propylene, produced from fossil fuels.

In recent years, increased efforts have focussed on producing chemicals, including glycols, from renewable feedstocks, such as sugar-based materials. The conversion of sugars to glycols can be seen as an efficient use of the starting materials with the oxygen atoms remaining intact in the desired product.

Current methods for the conversion of saccharides to sugars revolve around a hydrogenation/hydrogenolysis process as described in Angew. Chem. Int. Ed. 2008, 47, 8510-8513.

An important aim in this area is the provision of a process that is high yielding in desirable products, such as ethylene glycol and propylene glycol, and that can be carried out in a commercially viable manner. A preferred methodology for a commercial scale process would be to use continuous flow technology, wherein feed is continuously provided to a reactor and product is continuously removed therefrom. By maintaining the flow of feed and the removal of product at the same levels, the reactor content remains at a more or less constant volume.

Continuous flow processes for the production of glycols from saccharide feedstock have been described in US 2011/0313212, CN 102675045A, CN 102643165A, WO 2013/015955 and CN 103731258A. A process for the co-production of bio-fuels and glycols is described in WO 2012/174087.

Continuous flow processes may be carried out in a reactor operating in essentially a plug flow manner. In such a system there is little or no back-mixing. At the start of the reactor there will be a high concentration of reactants. The concentration of starting materials decreases as the material moves through the reactor as a 'plug' and the reaction proceeds. Problems occur when the high concentration of reactants causes decomposition and the formation of by-products, leading to reduced yields of the desired products.

A continuous flow process with a high degree of back mixing may be also carried out, for example, in a continuous flow stirred tank reactor. In such a system the concentration of reactants at any one point will be much reduced, preventing any decomposition due to high concentrations. However, in such a process, as some of the reaction mixture is continuously removed from the reactor, there will be some material that does not react to completion. This results in a product stream that contains starting material and/or intermediates, reducing the overall yield of the process and requiring separation of the starting material/intermediate from the desired product and disposal or recycling thereof.

It would, therefore, be advantageous to provide a continuous process for the preparation of ethylene glycol and 1,2-propylene glycol from saccharide containing feedstocks in which substantially full conversion of the starting material and/or intermediates is achieved and in which the formation of by-products is reduced.

SUMMARY OF THE INVENTION

Accordingly, the present invention provides a continuous process for the preparation of ethylene glycol and 1,2-propylene glycol from starting material comprising one or more saccharides, wherein the process comprises the steps of i) providing the starting material and hydrogen to a first reactor, which first reactor operates with mixing;
ii) reacting said starting material and hydrogen in the first reactor in the presence of solvent and a catalyst system;
iii) continuously removing a first reactor product stream from the first reactor;
iv) supplying at least a portion of the first reactor product stream to a second reactor, which reactor operates essentially in a plug flow manner; and
v) further reacting the first reactor product stream with hydrogen in the presence of a solvent and optionally a catalyst system in the second reactor.

DETAILED DESCRIPTION OF THE INVENTION

The present inventors have surprisingly found that using a multiple reactor system comprising a reactor with mixing followed by a reactor operating essentially with plug flow provides a process in which substantially complete conversion of saccharides can be achieved in the conversion of saccharides to ethylene glycol and 1,2-propylene glycol.

The starting material for the subject process comprises at least one saccharide selected from the group consisting of monosaccharides, disaccharides, oligosaccharides and polysaccharides. Examples of polysaccharides include cellulose, hemicelluloses, starch, glycogen, chitin and mixtures thereof. If the starting material comprises oligosaccharides or polysaccharides, it is preferable that it is subjected to pre-treatment before being fed to the reactor in a form that can be converted in the process of the present invention. Suitable pre-treatment methods are known in the art and one or more may be selected from the group including, but not limited to, sizing, drying, grinding, hot water treatment, steam treatment, hydrolysis, pyrolysis, thermal treatment, chemical treatment, biological treatment.

Preferably, the starting material supplied to the first reactor after any pre-treatment comprises one or more saccharide selected from the group consisting of glucose, sucrose and starch. Said saccharide is suitably present as a solution, a suspension or a slurry in the solvent.

The solvent may be water or a $C_1$ to $C_6$ alcohol or mixtures thereof. Preferably, the solvent is water. Further solvent may also be added to the reactor in a separate feed stream or may be added to the saccharide-containing feed stream before it enters the reactor. Said solvent is also suitably water or a $C_1$ to $C_6$ alcohol or mixtures thereof.

Preferably, both solvents are the same. More preferably, both solvents comprise water. Most preferably, both solvents are water.

In the process of the invention, the starting material is reacted with hydrogen in the presence of a catalyst system in the first reactor. Optionally, a catalyst system may also be present in the second reactor. In one embodiment of the invention, the second reactor is operated in the absence of a catalyst system. In such an embodiment, it is possible that some minor amount of catalyst system from the first reactor is present in the second reactor, but no catalyst system is provided in the second reactor.

If a catalyst system is present in the second reactor, the catalyst system used in each of the reactors may be the same or different. A further advantage of the invention is that different catalysts, tailored to the feed being supplied to each reactor, may be used in each reactor.

Each catalyst system and the components contained therein may be heterogeneous or homogeneous with respect to the solvent or solvents present in the reactors during the process of the present invention.

In one embodiment of the present invention, a homogeneous catalyst system is used in the first reactor. In this embodiment, the catalyst system may remain in the first reactor product stream and be supplied to the second reactor within that stream. Alternatively, a separation step may be included between the two reactors to allow any catalyst in the first reactor product stream to be separated and, optionally, recycled to the first reactor. A further, preferably different, catalyst system may then be present in the second reactor. This further catalyst system can be present in the second reactor as a heterogeneous system or may be another homogeneous catalyst system added to the second reactor, or the first reactor product stream before it enters the second reactor. Alternatively, no catalyst system may be present in the second reactor.

In another embodiment of the invention a heterogeneous catalyst system is used in the first reactor. In this embodiment, the second reactor may also contain the same or a different heterogeneous catalyst system or no catalyst system. Alternatively, the catalyst system present in the second reactor may be a homogeneous catalyst system added to the second reactor, or to the first reactor product stream before it enters the second reactor.

It should be readily understood that each catalyst system may also contain both heterogeneous and homogeneous components.

Depending on the physical state of the catalyst systems and any components contained therein, they may be pre-loaded into the reactors or, if they are in liquid form or present as a solution or slurry in a solvent, they may be fed into the reactor as required in a continuous or discontinuous manner during the process of the present invention.

In each reactor, the catalyst system used preferably comprises at least two active catalytic components comprising, as a first active catalyst component, one or more materials selected from transition metals from groups 8, 9 or 10 or compounds thereof, with catalytic hydrogenation capabilities; and, as a second active catalyst component, one or more materials selected from tungsten, molybdenum and compounds and complexes thereof.

Preferably, the first active catalyst component consists of one or more of the group selected from iron, cobalt, nickel, ruthenium, rhodium, palladium, iridium and platinum. This component may be present in the elemental form or as a compound. It is also suitable that this component is present in chemical combination with one or more other ingredients in the catalyst system. It is required that the first active catalyst component has catalytic hydrogenation capabilities and it is capable of catalysing the hydrogenation of material present in the reactor.

Preferably, the second active catalyst component comprises of one or more compound, complex or elemental material comprising tungsten, molybdenum, vanadium, niobium, chromium, titanium or zirconium. More preferably the second active catalyst component comprises one or more material selected from the list consisting of tungstic acid, molybdic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. Preferably, the second active catalyst component comprises one or more compound, complex or elemental material selected from those containing tungsten or molybdenum.

Preferably, at least one of the active catalyst components is supported on a solid support. In this embodiment, any other active catalyst component may be present in either heterogeneous or homogeneous form. Said any other active catalyst component may also be supported on a solid support. In one embodiment, the first active catalyst component is supported on one solid support and the second active catalyst component is supported on a second solid support which may comprise the same or different material. In another embodiment, both active catalyst components are supported on one solid support.

The solid supports may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

Suitably, the weight ratio of the first active catalyst component to the second active catalyst component is in the range of from 0.02:1 to 3000:1, preferably in the range of from 0.1:1 to 100:1, on the basis of the weight of metal present in each component. The weight ratio of the active catalyst components may be varied between the first and second reactors and it may be advantageous to alter the composition of the catalyst systems between the reactors to suit the different feed streams provided to each reactor.

The weight ratio of the first active catalyst component (based on the amount of metal in said component) to sugar is suitably in the range of from 1:100 to 1:1000. The weight ratio of the second active catalyst component (based on the amount of metal in said component) to sugar is suitably in the range of from 1:10 to 1:100.

The temperature in each of the reactors is suitably at least 130° C., preferably at least 150° C., more preferably at least 170° C., most preferably at least 190° C. The temperature in the reactor is suitably at most 300° C., preferably at most 280° C., more preferably at most 270° C., even more preferably at most 250° C. Preferably, the reactor is heated to a temperature within these limits before addition of any starting material and is maintained at such a temperature until all reaction is complete.

The pressure in each of the reactors is suitably at least 1 MPa, preferably at least 2 MPa, more preferably at least 3 MPa. The pressure in the reactor is suitably at most 12 MPa, preferably at most 10 MPa, more preferably at most 8 MPa. Preferably, the reactor is pressurised to a pressure within these limits by addition of hydrogen before addition of any starting material and is maintained at such a pressure until all reaction is complete through on-going addition of hydrogen.

Again, it may be advantageous to vary the conditions, e.g. temperature and pressure, between the first and second reactors. This can lead to a more tailored process to suit the different constituents of the feeds provided to each reactor.

The process of the present invention takes place in the presence of hydrogen. Preferably, the process of the present reaction takes place in the absence of air or oxygen. In order to achieve this, it is preferable that the atmosphere in the reactor be evacuated and replaced with hydrogen repeatedly, after loading of any initial reactor contents, before the reaction starts.

Mixing must occur in the first reactor. Said mixing should be carried out to such an extent that the concentrations of the materials in the reactor is relatively consistent throughout. The degree of mixing for a reactor is measured in terms of a Péclet number. An ideally-stirred tank reactor would have a Péclet number of 0. In the first reactor, the Péclet number is preferably at most 0.4, more preferably at most 0.2, even more preferably at most 0.1, most preferably at most 0.05.

It will be clear to the skilled person, however, that concentrations of any materials may be considerably higher or lower in the immediate vicinity of an inlet to the reactor. Suitable reactors to be used as the first reactor include those considered to be continuous stirred tank reactor may be used as the first reactor. Examples include slurry reactors, ebbulated bed reactors, jet flow reactors, mechanically agitated reactors, bubble columns, such as slurry bubble columns and external recycle loop reactors. The use of these reactors allows dilution of the reaction mixture to an extent that provides high degrees of selectivity to the desired glycol product (mainly ethylene and propylene glycols).

In a reactor operating with essentially a plug flow, all of the feed stream moves with the same radially uniform velocity and, therefore, has the same residence time. The concentration of the reactants in the plug flow reactor will change as it progresses through the reactor. Although the reaction mixture preferably essentially completely mixes in radial direction and preferably does essentially not mix in the axial direction (forwards or backwards), in practice some mixing in the axial direction (also referred to as back-mixing) may occur. Suitable reactors operating with essentially plug flow include, but are not limited to, tubular reactors, pipe reactors, falling film reactors, staged reactors, packed bed reactors and shell and tube type heat exchangers.

The plug flow reactor may for example be operated in the transition area between laminar and turbulent flow or in the turbulent area, such that a homogenous and uniform reaction profile is created.

A plug flow may for example be created in a tubular reactor. It may also be created in a compartmentalized tubular reactor or in another reactor or series of reactors having multiple compartments being transported forward, where preferably each of these compartments are essentially completely mixed. An example of a compartmentalized tubular reactor operated at plug flow may be a tubular reactor comprising a screw.

Preferably a Péclet number of at least 3, more preferably at least 6, and still more preferably at least 20, most preferably at least 100 is maintained within the plug flow reactor.

Such a reactor cannot typically be applied to the conversion of saccharides to ethylene glycol and propylene glycol as the concentration of saccharide at the inlet to the reactor and at the early points of the reactor would lead to an unacceptable high level of sugar degradation and fouling under the reaction conditions required.

Preferably at least 50 wt % of the starting material undergoes reaction in the first reactor. More preferably at least 70 wt %, even more preferably at least 80 wt %, even more preferably at least 90 wt %, most preferably at least 95 wt % of the starting material undergoes reaction in the first reactor.

The residence time in the first reactor is suitably at least 1 minute, preferably at least 2 minutes, more preferably at least 5 minutes. Suitably the residence time in the first reactor is no more than 5 hours, preferably no more than 2 hours, more preferably no more than 1 hour.

After further reacting the first reactor product stream with hydrogen in the presence of a solvent and a catalyst system in the second reactor in step (v) of the process of the invention, suitably at least 98 wt %, preferably at least 99 wt %, more preferably at least 99.5 wt % of the starting material has reacted to completion. Reacting to completion means that the starting material and any unsaturated components such as hydroxyl-ketones and hydroxyl-aldehydes are no longer present in the reaction mixture.

The present invention is further illustrated in the following Examples.

EXAMPLES

Example 1

30 ml deionized water, 0.300 g of a catalyst consisting of W(10.88)-Ni(3.63)-Pt(0.05) and $ZrO_2$ and 0.300 g of a catalyst consisting of Ru(1.0%) on $SiO_2$ catalyst were charged into a 60 ml autoclave equipped with a gas stirrer and hydrogen supply. The autoclave was closed, the gas phase was replaced by nitrogen, then by hydrogen and the autoclave was pressurised to 30 bara pressure. The autoclave was stirred at 1450 rpm, heated to 195° C. in 15 minutes and pressurised with hydrogen to 75 bara pressure. 5 ml of a solution of 20% wt glucose in water was fed to the reactor. After 5 minutes, a sample of 5 ml liquid is removed from the autoclave. The process of feeding and sampling is repeated for another 5 cycles in order to approximate the conditions in a continuous flow stirred tank reactor.

The reactor was then cooled to room temperature in 15 minutes, depressurized, opened, and the reactor content was filtered. 30 ml of reactor liquid with an average initial concentration of 12% w glucose is obtained. In addition, 30 ml combined sample liquid with an average initial concentration of 8% wt glucose is obtained. Yields of MEG, MPG and 1,2-butanediol (1,2-BDO) were quantified by GC-FID, applying a CPSi1-5 column and can be seen in Table 1.

TABLE 1

| Glucose, cumulative (% w) | MEG yield (% w) | MPG yield (% w) | 1,2-BDO yield (% w) |
|---|---|---|---|
| 12.0 (reactor liquid) | 14.45 | 1.11 | 1.06 |
| 8.0 (Combined 6 × 5 ml sample liquid) | 14.07 | 1.07 | 1.05 |

Example 2

The reactor liquid (30 ml) from Example 1 and 0.300 g of a Ru(1.0)/SiO$_2$ catalyst were charged into a 60 ml autoclave equipped with a gas stirrer and hydrogen supply. The autoclave was closed, and the gas phase was replaced by nitrogen, then by hydrogen. The autoclave was then pressurized to 30 bara. The autoclave was stirred at 1450 rpm, heated to 195° C. in 15 minutes, pressurised to 85 bara and kept at reaction conditions for 75 minutes. Such conditions are representative of a plug flow reactor. The reactor was then cooled down to room temperature in 15 minutes, depressurised, opened and a liquid sample was taken for analysis. Yields of MEG, MPG and 1,2-butanediol (1,2-BDO) have been quantified by GC-FID, applying a CPSi1-5 column. Yields are shown in Table 2.

Example 3

The filtered combined sample liquid (30 ml) from Example 1 and 0.200 g of a Ru(1.0)/SiO$_2$ catalyst were charged into a 60 ml autoclave equipped with a gas stirrer and hydrogen supply. The autoclave was closed, and the gas phase was replaced by nitrogen, then by hydrogen. The autoclave was pressurized to 30 bara. The autoclave was stirred at 1450 rpm, heated to 195° C. in 15 minutes, pressurised to 85 bara and kept at reaction conditions for 75 minutes. The reactor was then cooled to room temperature in 15 minutes, depressurised, opened and a liquid sample was taken for analysis. Yields of MEG, MPG and 1,2-butanediol (1,2-BDO) have been quantified by GC-FID, applying a CPSi1-5 column. Yields are shown in Table 2.

TABLE 2

| Glucose, cumulative (% w) | MEG yield (% w) | MPG yield (% w) | 1,2-BDO yield (% w) |
|---|---|---|---|
| 12.0 (Example 2) | 19.25 | 6.16 | 4.47 |
| 8.0 (Example 3) | 25.51 | 7.21 | 5.03 |

Example 4

15 ml of the filtrate from Example 2, 0.350 g of a W(10.88)-Ni(3.63)-Pt(0.05)/ZrO$_2$ catalyst and 0.350 g of a Ru(1.0)/SiO$_2$ catalyst were charged into a 60 ml autoclave equipped with a gas stirrer and hydrogen supply. The autoclave was closed, the gas phase replaced by nitrogen, then by hydrogen and the autoclave was then pressurised to 30 bara. The autoclave was stirred at 1450 rpm and heated to 195° C. in 12-15 minutes. The autoclave was kept at 195° C. while a solution of 4.2 g glucose dissolved in 15 ml deionised water was fed hot to the reactor. The pressure of reactor was adjusted to 85 bara. The total amount of glucose intake is 6 gram, corresponding to a cumulative concentration of 20% wt glucose. Samples were removed after 1 minute and 5 minutes of reaction and the reaction was then allowed to continue for 75 minutes. The reactor was then cooled to room temperature in 15 minutes, depressurised, opened, a liquid sample of 0.3 ml was taken for analysis, yields of MEG, MPG and 1,2-butanediol (1,2-BDO) were quantified by GC-FID, applying a CPSi1-5 column. Yields are shown in Table 3.

TABLE 3

| sample | MEG yield (% w) | MPG yield (% w) | 1,2-BDO yield (% w) |
|---|---|---|---|
| 1 minute | 1.62 | 0.76 | 1.07 |
| 5 minutes | 8.09 | 1.74 | 1.85 |
| 75 minutes | 16.79 | 6.1 | 4.8 |

Example 5

15 ml of filtrate from Example 3, 0.400 g of a W(10.88)-Ni(3.63)-Pt(0.05)/ZrO$_2$ catalyst and 0.400 g of a Ru(1.0)/SiO$_2$ catalyst were charged into a 60 ml autoclave equipped with a gas stirrer and hydrogen supply. The autoclave was closed, the gas phase was replaced by nitrogen, then by hydrogen and the autoclave was pressurised to 30. The autoclave was stirred at 1450 rpm, heated to 195° C. in 12-15 minutes. The reaction temperature was maintained at 195° C. and a solution of 4.8 g glucose dissolved in 15 ml deionised water was fed hot to the reactor. The total amount of glucose intake was 6 g, corresponding to a cumulative concentration of 20% wt glucose. The pressure of reactor was adjusted to 85 bara. Samples were removed after 1 minute and 5 minutes of reaction and the reaction was allowed to continue for 75 minutes. The reactor was then cooled to room temperature in 15 minutes, depressurised, opened and a liquid sample of 0.3 ml was taken for analysis, yields of MEG, MPG and 1,2-butanediol (1,2-BDO) have been quantified by GC-FID, applying a CPSi1-5 column (Table 4).

TABLE 4

| sample | MEG yield (% w) | MPG yield (% w) | 1,2-BDO yield (% w) |
|---|---|---|---|
| 1 minute | 7.41 | 1.57 | 1.68 |
| 5 minutes | 6.2 | 1.47 | 1.63 |
| 75 minutes | 17.23 | 6.0 | 4.68 |

That which is claimed is:

1. A process for the preparation of ethylene glycol and 1,2-propylene glycol from starting material comprising one or more saccharides, wherein the process comprises the steps of
   i) providing the starting material and hydrogen to a first reactor, which first reactor operates with mixing;
   ii) reacting said starting material and hydrogen in the first reactor in the presence of solvent and a catalyst system;
   iii) continuously removing a first reactor product stream from the first reactor;
   iv) supplying at least a portion of the first reactor product stream to a second reactor, which reactor operates essentially in a plug flow manner; and
   v) further reacting the first reactor product stream with hydrogen in the presence of a solvent and, optionally, a catalyst system in the second reactor.

2. A process according to claim 1, wherein the catalyst systems present in the first and second reactor each individually and independently comprise at least two active catalytic components comprising, as a first active catalyst component, one or more materials selected from the group consisting of transition metals from groups 8, 9 or 10 or compounds thereof, with catalytic hydrogenation capabilities; and, as a second active catalyst component, one or more materials selected from the group consisting of tungsten, molybdenum, tungsten or molybdenum containing compounds and complexes of tungsten or molybdenum.

3. A process according to claim 1, wherein the starting material comprises one or more saccharide selected from the group consisting of glucose, sucrose and starch.

4. A process according to claim 1, wherein the first reactor is maintained with a Peclet number of at most 0.4.

5. A process according to claim 1, wherein the first reactor is selected from the group consisting of slurry reactors ebbulated bed reactors, jet flow reactors, mechanically agitated reactors, bubble columns and external recycle loop reactors.

6. A process according to claim 1, wherein the second reactor is maintained with a Peclet number of at least 3.

7. A process according to claim 1, wherein the second reactor is selected from the group consisting of tubular reactors, pipe reactors, falling film reactors, staged reactors, packed bed reactors and shell and tube type heat exchangers.

8. A process according to claim 1, wherein at least 95 wt % of the starting material undergoes reaction in the first reactor.

9. A process according to claim 1, wherein after step v), at least 98 wt % of the starting material has reacted to completion.

* * * * *